(12) United States Patent
van Alphen et al.

(10) Patent No.: US 12,702,778 B2
(45) Date of Patent: Aug. 11, 2026

(54) TRACHEOSTOMA DEVICE HOLDER

(71) Applicant: Coloplast A/S, Humlebaek (DK)

(72) Inventors: Maarten Jan Antony van Alphen, Amsterdam (NL); Maartje Leemans, Gouda (NL); Edsko Evert Geert Hekman, Enschede (NL); Richard Dirven, Nijmegen (NL)

(73) Assignee: Coloplast A/S, Humlebaek (DK)

( * ) Notice: Subject to any disclaimer, the term of this patent is extended or adjusted under 35 U.S.C. 154(b) by 782 days.

(21) Appl. No.: 17/927,705

(22) PCT Filed: May 31, 2021

(86) PCT No.: PCT/SE2021/050503
§ 371 (c)(1),
(2) Date: Nov. 24, 2022

(87) PCT Pub. No.: WO2021/246938
PCT Pub. Date: Dec. 9, 2021

(65) Prior Publication Data

US 2023/0211102 A1 Jul. 6, 2023

(30) Foreign Application Priority Data

Jun. 2, 2020 (SE) .................................... 2050635-8

(51) Int. Cl.
*A61M 16/04* (2006.01)

(52) U.S. Cl.
CPC . *A61M 16/0468* (2013.01); *A61M 2205/0216* (2013.01)

(58) Field of Classification Search
CPC ........................................ A61M 16/0465–047
See application file for complete search history.

(56) References Cited

U.S. PATENT DOCUMENTS 3,330,271 A 7/1967 Hozier
4,040,428 A * 8/1977 Clifford ............ A61M 16/0468 623/9
5,464,011 A 11/1995 Bridge
6,971,382 B1 * 12/2005 Corso ..................... A61F 2/203 128/207.29
7,025,784 B1 * 4/2006 Blom ...................... A61F 2/203 623/14.11
7,506,647 B2 3/2009 Worthington
2004/0187941 A1 * 9/2004 Seder ..................... F16K 15/16 137/855

(Continued)

FOREIGN PATENT DOCUMENTS

CA 2353007 A1 6/2000
DE 202006005101 U1 6/2006

(Continued)

*Primary Examiner* — Rachel T Sippel
(74) *Attorney, Agent, or Firm* — Coloplast Corp., Coloplast A/S; Nick Baumann

(57) ABSTRACT

A tracheostoma device holder (10) for holding a tracheostoma device to a tracheostoma of a person is provided. The tracheostoma device holder (10) comprises a head portion (50) for engaging with a tracheostoma device and a fixation portion (20) for fixating the tracheostoma device holder (10) to the tracheostoma of the person. At least a portion of the fixation portion (20) is provided with a deformable material (60).

20 Claims, 8 Drawing Sheets

(56) References Cited

U.S. PATENT DOCUMENTS

2008/0033366 A1* 2/2008 Matson ............... A61L 24/0036
604/533
2008/0275402 A1 11/2008 Schnell
2012/0167893 A1 7/2012 Schulz et al.
2013/0319405 A1 12/2013 Perry
2015/0083119 A1 3/2015 Persson
2017/0319803 A1* 11/2017 Aho .................. A61M 16/0465
2019/0111225 A1 4/2019 Selveo et al.

FOREIGN PATENT DOCUMENTS

DE 202015002407 U1 4/2015
DE 202016003641 U1 7/2016
DE 202017000842 U1 3/2017
EP 3153201 A2 4/2017
GB 2349341 B 5/2003
WO 2000066208 A2 11/2000
WO 2016097383 A1 6/2016
WO 2016115211 A1 7/2016
WO 2020067980 A1 4/2020
WO 2020099813 A1 5/2020

* cited by examiner

TRACHEOSTOMA DEVICE HOLDER

FIELD OF THE INVENTION

This invention pertains in general to a tracheostoma device holder. More particularly, the present invention pertains to a tracheostoma device holder for holding a tracheostoma device to a tracheostoma of a person. The tracheostoma device holder comprises a head portion for engaging with a tracheostoma device and a fixation portion for fixating the tracheostoma device holder to the tracheostoma of the person.

BACKGROUND OF THE INVENTION

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a person has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the person to speak. It is desirable that the flow of the exhaled air be controlled by means of a tracheostoma valve. In these situations, the valve can be arranged to remain open during breathing but can be closed to divert the airflow, through a small additional increase in exhaled air flow.

In this respect, tracheostoma devices, such as filter devices, Heat and Moisture Exchanger (HME), breathing protectors, and speech valves, have been developed to enable moisturizing of inhaled air, removal of small particles and bacteriological substances in said inhaled air, and providing the person with the ability to speak by closing the air passage through the tracheostoma by manual operation. As an alternative, some use a "hands free" HME (automatic speaking valve) that is activated by speaking. A hands-free HME enables laryngectomees to speak without requiring finger occlusion. The device consists of a combination of HME and an automatic speaking valve, which closes automatically, when exhaling air for speaking, enabling the pulmonary air to be diverted through the voice prosthesis into the esophagus. It reopens automatically, when exhalation decreases.

These tracheostoma devices are arranged to be held to the tracheostoma by fixation devices or tracheostoma device holders. The tracheostoma device is arranged to have one part engaged with the person using the tracheostoma device and one part arranged to engage with the tracheostoma device. The part that is arranged to engage with the person using the tracheostoma device generally uses either peristomal, i.e. around the stoma, or intratracheal, inside the stoma, fixation methods.

However, there are problems associated with tracheostoma device holders. They may be very uncomfortable to use. The tracheostoma device holders have a non-functional shape and poor fit due to large differences in tracheostoma morphology between persons. There is no average tracheostoma morphology and therefore it is not possible to make a customized tracheostoma device holder that fits all tracheostomas. In addition to this, the tracheostoma device holders may also be very uncomfortable due to stiff materials, constant pressure and possible skin and mucosa irritations. The fixation of the tracheostoma device can lead to traumatization of the peristomal or tracheal tissue. In addition to this, the tracheostoma device holders limit the mobility of the neck.

A bad fit of the tracheostoma device holder may be not only uncomfortable, it may also lead to dislodgement of the tracheostoma device. A bad fit between the tracheostoma and the tracheostoma device may lead to air leakages. These are major problems when using automatic speaking valves, especially during use of hands-free speech. Automatic speaking valves exert more stress on the fixation devices than manually closed filters, therefore, an optimal airtight seal is necessary to withstand the pressure and enable hands-free speech.

Hence, an improved tracheostoma device holder would be advantageous, and in particular a tracheostoma device holder allowing for increased user comfort including a good fit with an airtight seal.

SUMMARY OF THE INVENTION

Accordingly, the present invention preferably seeks to mitigate or eliminate one or more of the above-identified deficiencies and disadvantages, singly or in any combination, and solves at least the above mentioned problems by providing a tracheostoma device holder for holding a tracheostoma device to a tracheostoma of a person. Said tracheostoma device holder comprises a head portion for engaging with a tracheostoma device and a fixation portion for fixating the tracheostoma device holder to the tracheostoma of the person. At least a portion of an exterior surface of the fixation portion is provided with a deformable material. The deformable material will provide a deformable fixation surface and seal between the tracheostoma device holder and the tracheostoma walls of the tracheostoma.

Thereby, a tracheostoma device holder, which can become suitable for a wider range of tracheostoma shapes, which has an increased user comfort, strength and airtightness of intratracheal fixation, is provided.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF THE EMBODIMENTS

The following description focuses on an embodiment of the present invention applicable to a tracheostoma device holder for holding a tracheostoma device to a tracheostoma of a person. A tracheostoma device may in this context be an HME, speech valve, etc.

Figure 1A:
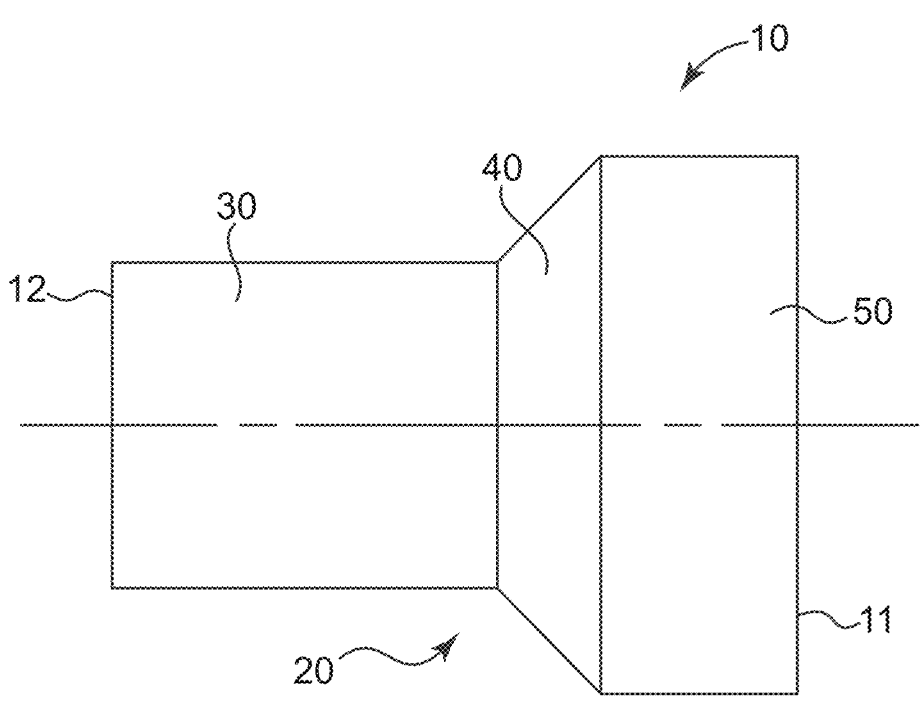
FIG. 1*a* is a side view of a tracheostoma device holder.
Figure 1B:
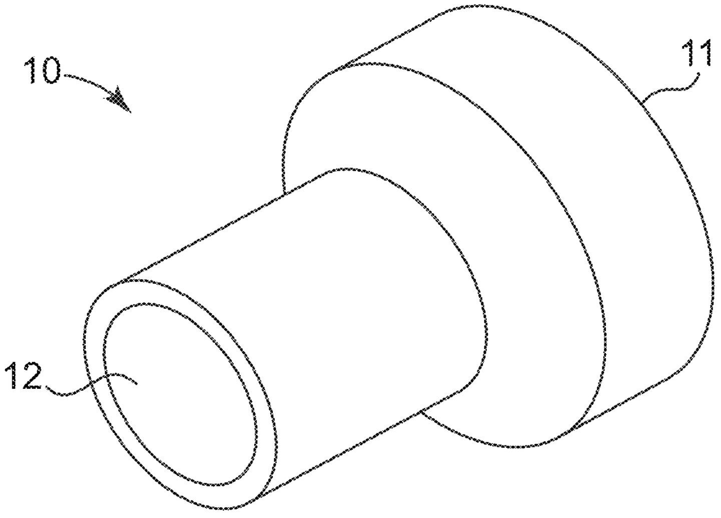
FIG. 1*b* is a perspective view of a tracheostoma device holder.

FIG. 1*a* discloses a tracheostoma device holder 10 for holding a tracheostoma device to a tracheostoma of a person. The tracheostoma device holder 10 comprises a head portion 50 for engaging with a tracheostoma device. The tracheostoma device holder 10 further comprises a fixation portion 20 for fixating, or sealing, the tracheostoma device holder 10 to the tracheostoma of a person. FIG. 1*b* illustrates a perspective view of such tracheostoma device holder 10.

Figure 2A:
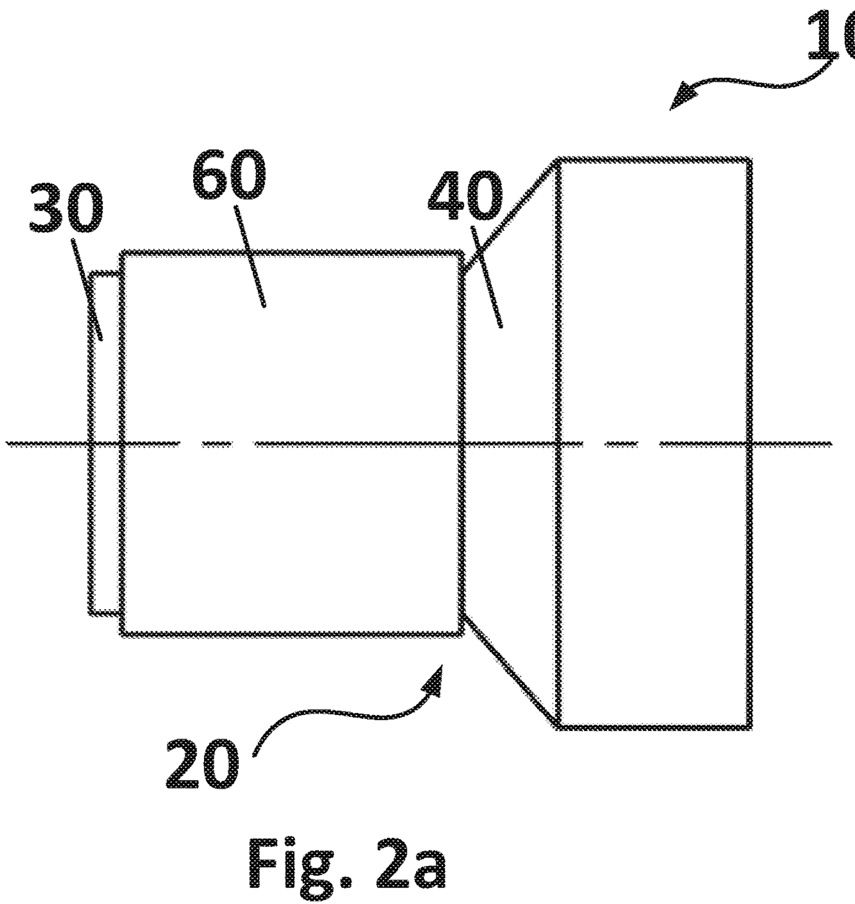
FIG. 2*a* is a side view of a tracheostoma device holder according to an embodiment of the present invention.
Figure 2B:
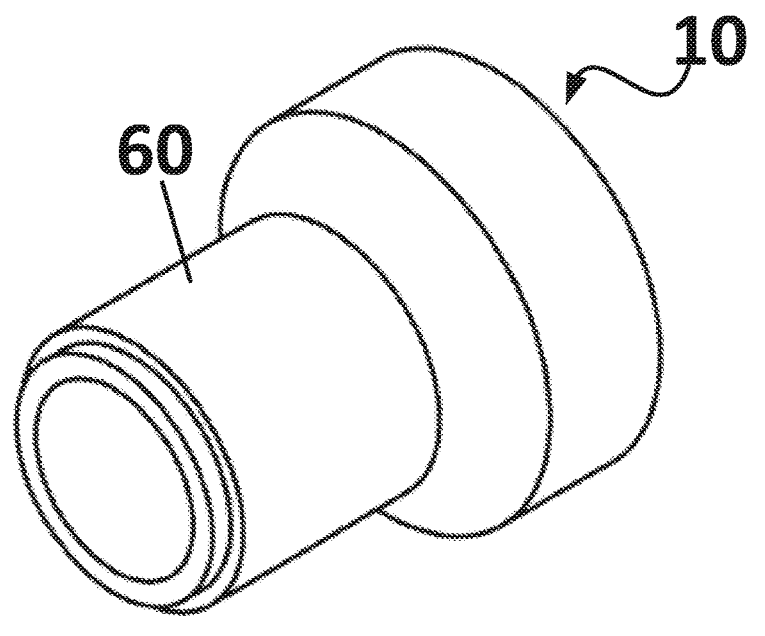
FIG. 2*b* is a perspective view of a tracheostoma device holder according to an embodiment of the present invention.

FIG. 2*a* illustrates a first embodiment according to the present invention. Similar as described with reference to FIG. 1*a* and FIG. 1*b*, the tracheostoma device holder 10 according to the present invention comprises a head portion 50 for engaging with a tracheostoma device and a fixation portion 20 for fixating the tracheostoma device holder 10 to the tracheostoma of a person. According to the present disclosure, at least a portion of an exterior surface of the fixation portion 20 is provided with a deformable material 60. The deformable material may be an expandable Polyvinyl Alcohol (PVA) foam. As also seen in FIG. 2*a*, the deformable material 60 is arranged on the exterior surface of the fixation portion 20, i.e. on an exterior side of the fixation portion 20, which surface is facing towards the tracheostoma. The deformable material 60 of the fixation portion 20 is arranged such that the deformable material 60 will be exposed to the tracheostoma when the tracheostoma device holder 10 is fixated to the tracheostoma.

When the tracheostoma device holder 10 is not in use, the deformable material 60 is not deformed. As previously described, an example of a deformable material 60 may be an expandable PVA foam 60. In such example embodiment, the PVA foam may be a dry hydrophilic PVA foam when the tracheostoma device holder 10 is not in use. An example of a tracheostoma device holder 10 provided with a dry PVA foam 60 is illustrated in FIG. 2*a*. The dry hydrophilic PVA foam 60 will expand under influence of fluids such as moisture from exhaled air and mucus in a tracheostoma environment. Thus, when the tracheostoma device holder 10, or more specifically the fixation portion 20 provided with the PVA foam 60, is placed to, or inside, the tracheostoma for fixation, the PVA foam 60 will attract moisture and expand. The PVA foam 60 may expand fully within minutes when arranged at the tracheostoma. The expanded PVA foam 60, located exterior of the fixation portion 20, will provide a deformable fixation surface and seal between the tracheostoma device holder 10 and the tracheostoma walls of the tracheostoma.

Figure 2C:
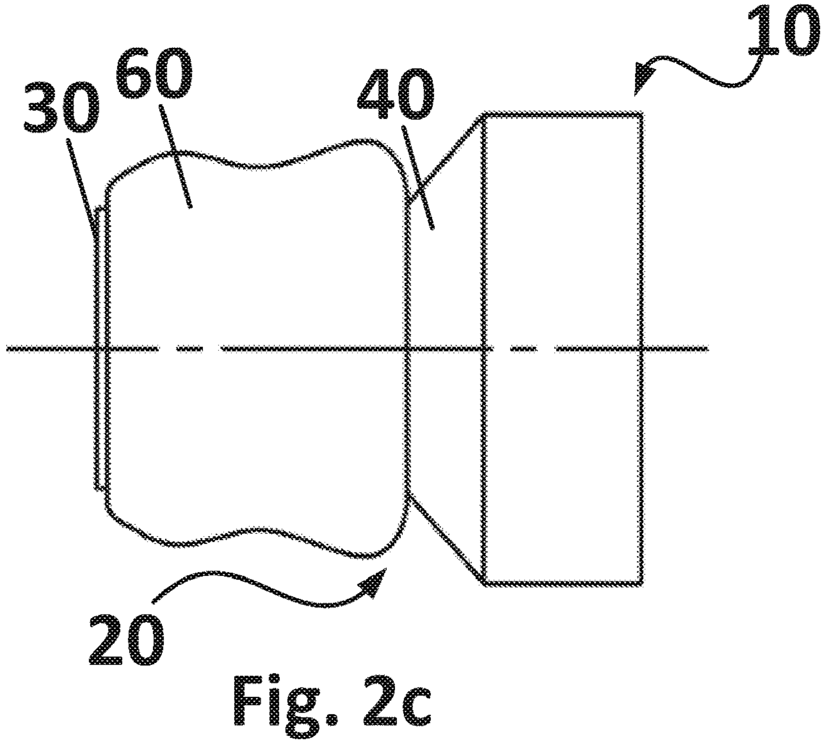
FIG. 2*c* is a side view of a tracheostoma device holder according to an embodiment of the present invention.

FIG. 2*c* illustrates an example embodiment of a tracheostoma device holder 10 with a deformed deformable material 60. The deformed deformable material 60 illustrated in FIG. 2*c* may be, for example, an expanded PVA foam 60, i.e. a PVA foam 60 that has attracted moisture. The expanded PVA foam 60 is deformable and will thus adapt to the tracheostoma. Due to the deformable material 60, it is possible to use one type of tracheostoma device holder 10 for tracheostoma of different sizes and shapes and thus reducing the need of a user specific customization. As the material 60 is deformable, it also provides a good fit to the tracheostoma without exerting excessive pressure on the trachea wall. Without excessive pressure, the risk of pain or ischaemic damage may be eliminated, or at least reduced. One of the most important hazards when using tracheostoma device holders 10 is indirect trauma caused by constant pressure on the tracheal mucosa, leading to ischaemic damage. The soft tissue of the trachea wall is capable of sustaining pressure for a small duration of time. However, when the pressure is exerted for a longer period of time, or above the capillary filling pressure of 32 mmHg, it can cause occlusion or decrease of mucosal perfusion, also known as ischemia. When ischemia persists, ischaemic damage can occur within a few hours. However, this problem is addressed by providing a fixation portion 20 with a deformable material 60, such as a PVA foam 60. Accordingly, a comfortable tracheostoma device holder 10 is presented, which provides a very good fit to the tracheostoma without exerting excessive pressure on the trachea wall that may cause pain or ischaemic damage. The provided tracheostoma device holder 10 is comfortable to wear and allows natural movement of the trachea and neck. Additionally, the fixation portion 20, wherein at least a portion of the exterior surface is provided with the deformable material 60, may also provide a sealing function and may give an increased and comfortable airtight fixation inside the tracheostoma during automatic speaking valve hands-free speech.

Figure 2D:
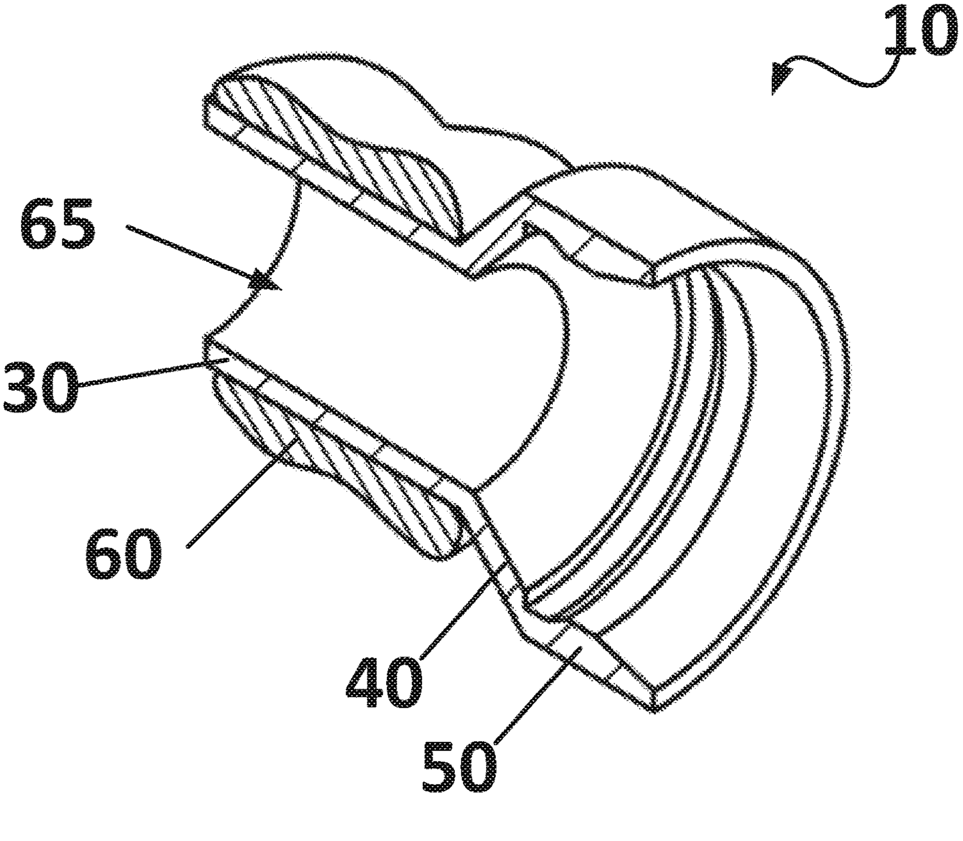
FIG. 2*d* is a cross-section view of a tracheostoma device holder according to an embodiment of the present invention.

As illustrated in FIG. 2*d*, the tracheostoma device holder 10 is provided with a through hole, or breathing lumen, 65. As may be appreciated, the hole 65 is provided to allow air to flow through the tracheostoma device holder 10. Thus, all different portions of the tracheostoma device holder 10 according to the present disclosure are provided with the hole 65 in the centre. Accordingly, in use an air flow will pass from the surroundings of the person wearing the tracheostoma device holder 10, through the tracheostoma device holder 10, into the trachea of said person. Thus, the tracheostoma device holder 10 comprises a distal opening 11 communicating with a proximal opening 12 in the tracheostoma device holder 10. This is also illustrated in FIG. 1*a*.

In some embodiments, as illustrated in FIG. 2*a*-*d*, the fixation portion 20 of the tracheostoma device holder 10 comprises an elongated tube portion 30 and a radially expanding portion 40. The elongated tube portion 30 may be configured for tracheostoma insertion through the tracheostoma into the trachea. By providing a fixation portion 20 comprising a tube portion 30 and a radially expanding portion 40, the tracheostoma device holder 10 may easily be inserted into the tracheostoma of a person intending to use the tracheostoma device holder 10. The tracheostoma device holder 10 may thus provide intratracheal fixation, which may make it possible to fixate the tracheostoma device holder 10 using an intratracheal fixation method. By using intratracheal fixation, the need of extra peristomal fixation is eliminated, or at least reduced. This may increase the comfort of the person using the tracheostoma device holder 10.

Figure 3:
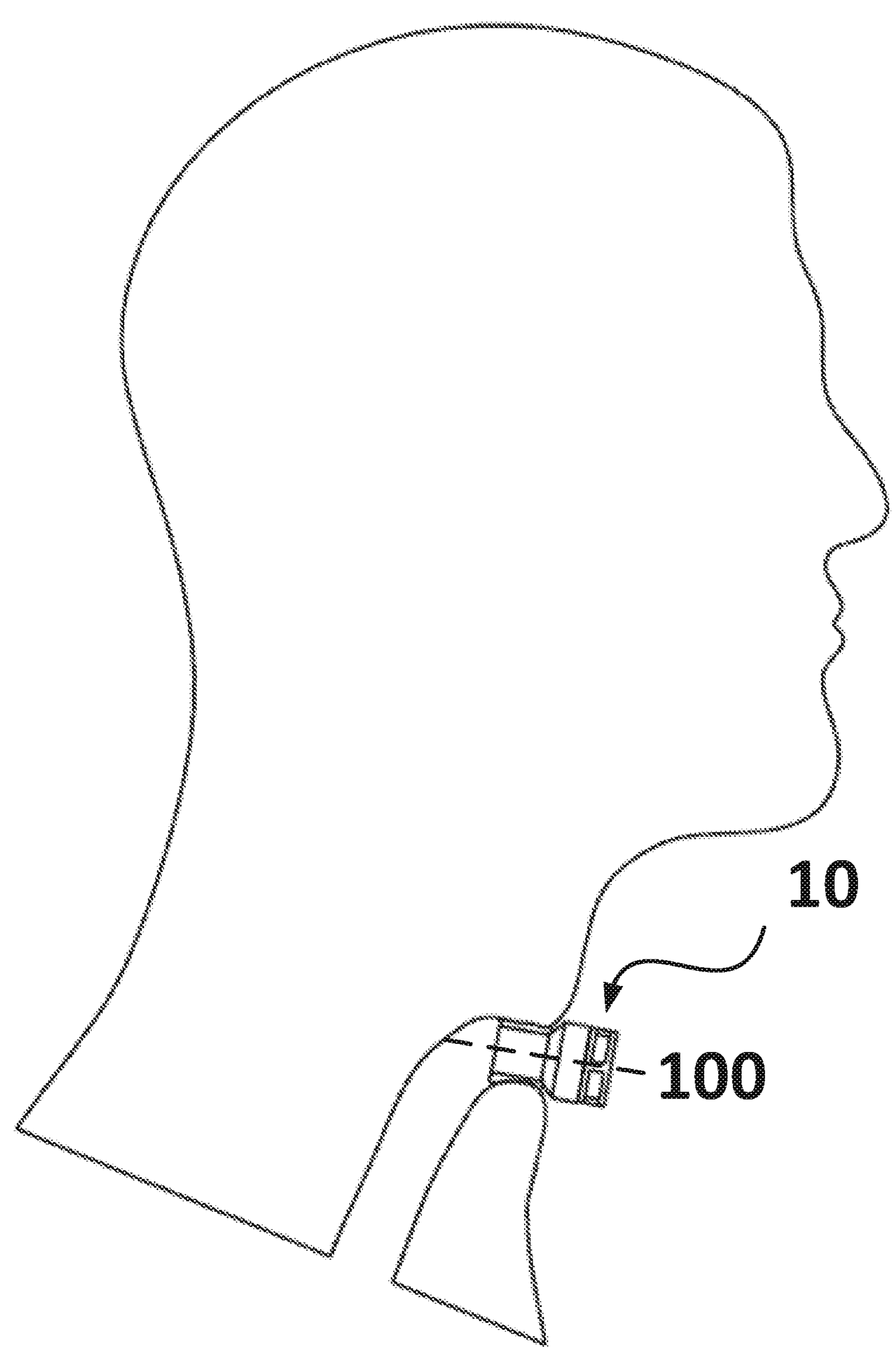
FIG. 3 illustrates a tracheostoma device holder according to an embodiment of the present invention in use.

FIG. 3 illustrates a tracheostoma device holder 10 according to the present disclosure attached to a person. As seen in FIG. 3, the tracheostoma device holder 10 is using an intratracheal fixation method as describe above. As previously described, by using a tracheostoma device holder 10 with intratracheal fixation, the need of using extra peristomal fixation is eliminated, or at least reduced. For example, the use of adhesive baseplates potentially irritating the peristomal skin may be avoided. Additionally, bulky holding devices around the neck of a person may be eliminated, or at least reduced. The tracheostoma device holder 10 may stay fixated to the tracheostoma without dislodging during loud speech and coughing. According to these embodiments, the tracheostoma device holder 10 may additionally be used as a tracheostoma button. The tracheostoma button may be configured to maintaining the tracheostoma open.

As also illustrated in FIG. 3, the tracheostoma device holder 10 according to the present disclosure comprises a proximal end and a distal end. In this context proximal refers to a position or direction towards the stoma, i.e. towards the user of the tracheostoma device holder 10, whilst distal refers to a position or direction away from the stoma, i.e. away from the user of the tracheostoma device holder 10. Thus, the fixation portion 20 is located at the proximal end of the tracheostoma device holder 10, while the head portion 50 is located at the distal end of the tracheostoma device holder 10. In embodiments where the fixation portion 20 comprises a tube portion 30 and a radially expanding portion 40, the tube portion 30 is located at the proximal end of the tracheostoma device holder 10. Exterior refers to a position, or direction, radially away from an axis 100 of the through hole 65, whilst central refers to a position or direction towards the central axis 100. Thus, the exterior surface of the fixation portion 20 is the surface facing the tracheostoma and the radially expanding portion 40 expands in an exterior, or outward, direction. The axis 100 extends in a distal-proximal direction through the tracheostoma device holder 10. With advantage said axis 100 may coincide with a central axis of said tracheostoma device holder 10.

As seen in FIG. 2*d*, the radially expanding portion 40 is connected to the tube portion 30 at one end and connected to the head portion 50 of the tracheostoma device holder 10 at the other end. The tube portion 30, the radially expanding portion 40 and the head portion 50 may preferably be integrally formed and manufactured as one integral and monolithic body. By manufacturing the tube portion 30, the radially expanding portion 40 and the head portion 50 as one integral body, the number of production steps is reduced, as the different portions, or parts, do not have to be joined together and only one material for all the portions has to be chosen. The production process may be simplified as the parts may be manufactured together in one process. Furthermore, by eliminating the interface between tube portion 30, the radially expanding portion 40 and the head portion 50, there may be less risk of the interface between the parts to break, as there will not exist an interface.

The tracheostoma device holder 10 is made out of a medical grade material, preferably matching the stiffness of the surrounding biological tissue. The tracheostoma device holder 10 is preferably made of silicone rubber. The silicone rubber of the tracheostoma device holder 10 has a Young's modulus close to that of the natural tracheal mucosa. Silicone rubber has advantageous safety properties, such as biocompatibility and durability. It is non-toxic and does not trigger allergic reactions.

Figure 4A:
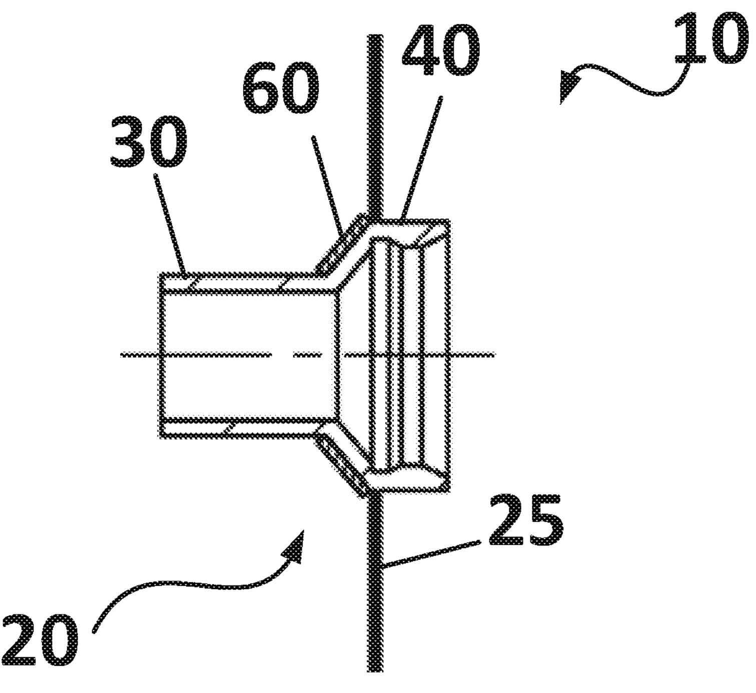
FIG. 4*a-c* are cross-section views of a tracheostoma device holder according to an embodiment of the present invention.
Figure 4B:
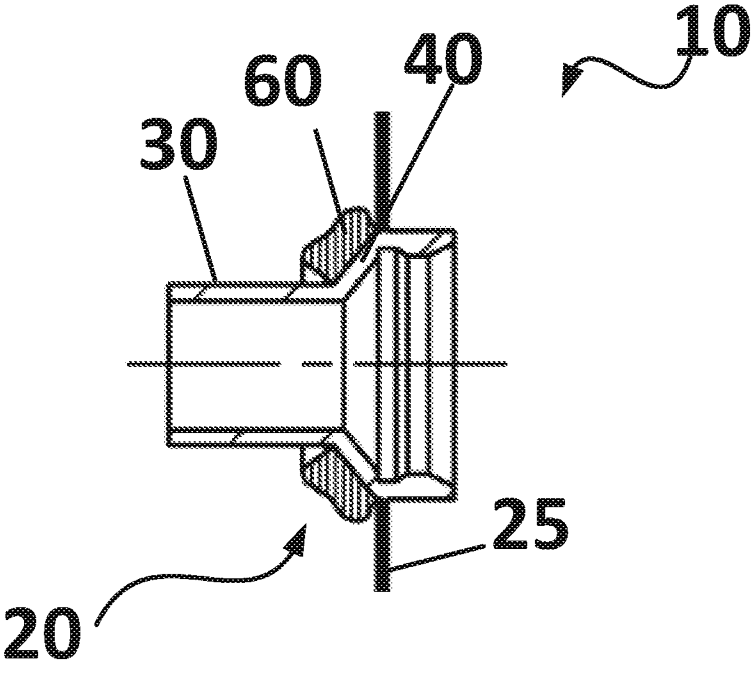
Figure 4C:
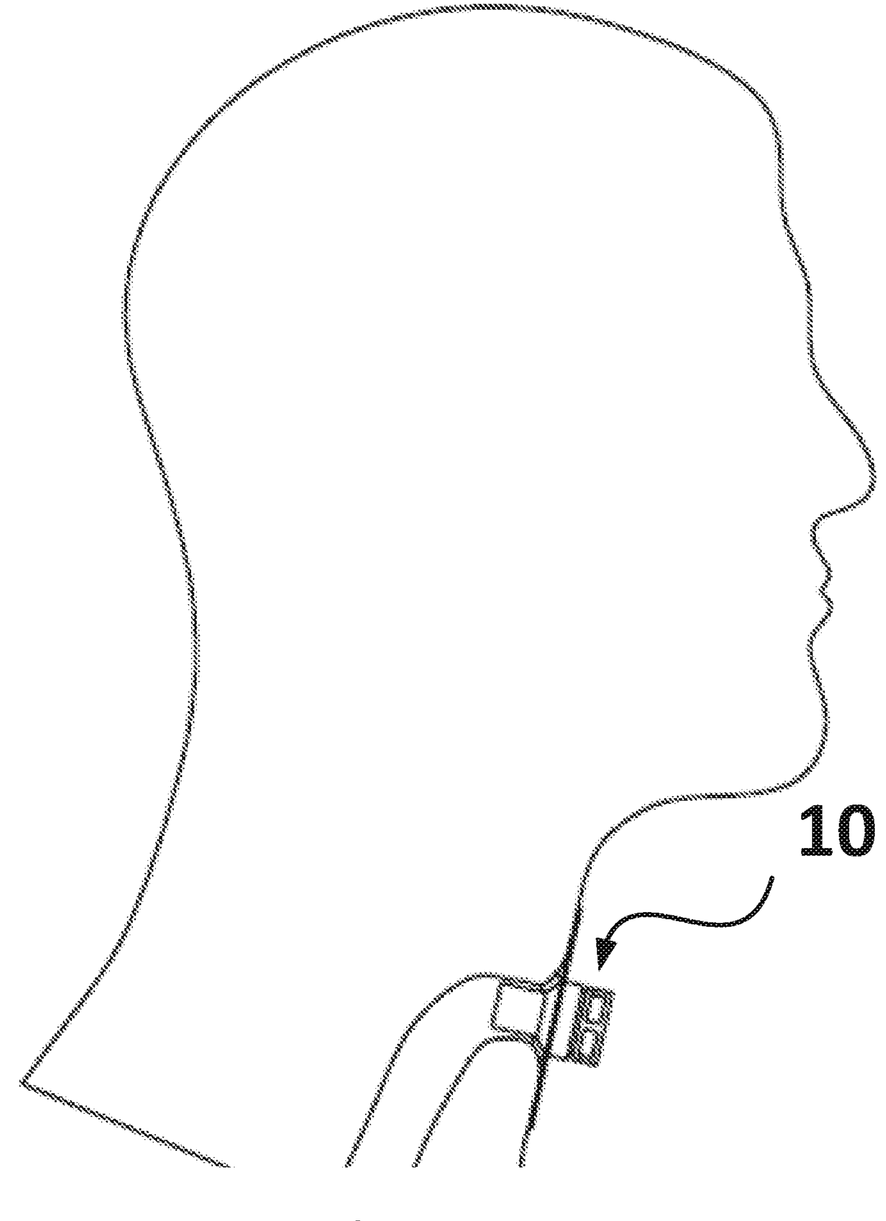

As previously described, at least a portion of the exterior surface of the fixation portion 20 is provided with a deformable material 60, such as an expandable PVA foam. The fixation portion 20 illustrated in FIG. 2*a*-*d* comprises a tube portion 30 and a radially expanding portion 40. In FIG. 2*a*-*d*, at least a portion of the fixation portion 20 provided with deformable material 60 corresponds to at least a portion of the tube portion 30. Thus, in these embodiments, the deformable material 60 is only provided to at least a portion of the tube portion 30. According to other embodiments, as also illustrated in FIG. 4*a*, at least a portion of the exterior surface of the fixation portion 20 corresponds to at least a portion of the radially expanding portion 40. Thus, according to these embodiments, at least a portion of the radially expanding portion 40 is provided with the deformable material 60. In FIGS. 4*a* and 4*b*, the deformable material is exemplified as an expandable PVA foam. FIG. 4*a* illustrates the tracheostoma device holder 10 with a dry PVA foam 60, and FIG. 4*b* illustrates the tracheostoma device holder 10 with an expanded PVA foam 60. FIG. 4*c* illustrates the tracheostoma device holder 10 according to these embodiments in use. In FIG. 4*a*-*c*, when at least a portion of the radially expanding portion 40 is provided with the deformable material 60, the deformable material 60 may act primarily as a sealing function. As illustrated in FIG. 4*a*-*c*, according to these embodiments, the fixation portion 20 of the tracheostoma device holder 10 may further comprise an adhesive baseplate 25. The adhesive baseplate 25 may ensure that the tracheostoma device holder 10 is kept in place.

In the embodiments illustrated in FIG. 2*a*-*d* and FIG. 4*a*-*c*, a portion of the respective portions, i.e. the tube portion 30 and the radially expanding portion 40, are provided with the deformable material 60. However, it may be appreciated that at least a portion of the exterior surface of these portions also covers embodiments where the total exterior surface of the insertion portion 30 or the radially expanding portion 40 may be provided with the deformable material 60.

Figure 5A:
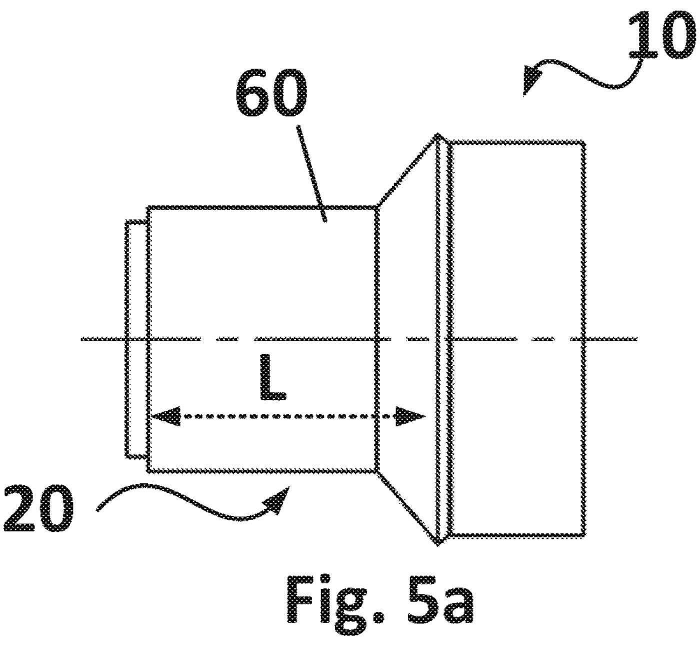
FIG. 5*a* is a side view of a tracheostoma device holder according to an embodiment of the present invention.
Figure 5B:
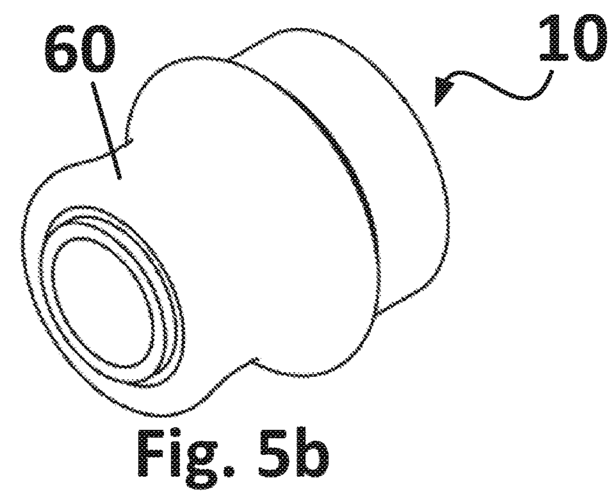
FIG. 5*b* is a perspective view of a tracheostoma device holder according to an embodiment of the present invention.
Figure 5C:
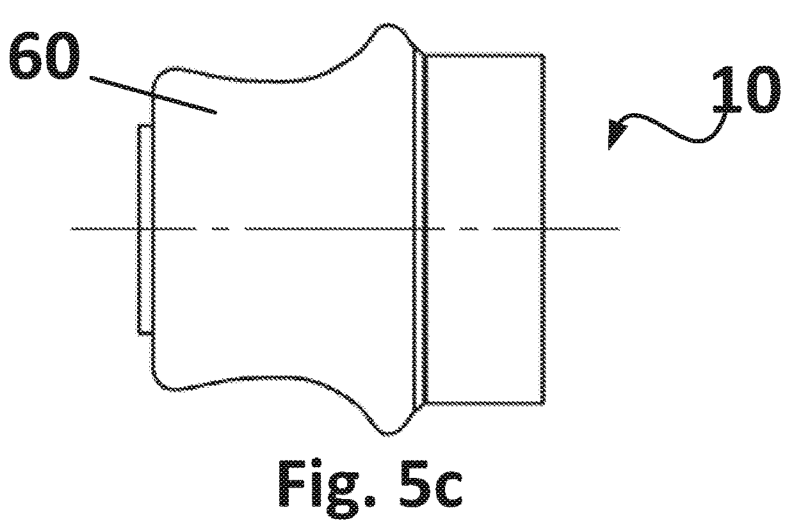
FIG. 5*c* is a side view of a tracheostoma device holder according to an embodiment of the present invention.
Figure 6:
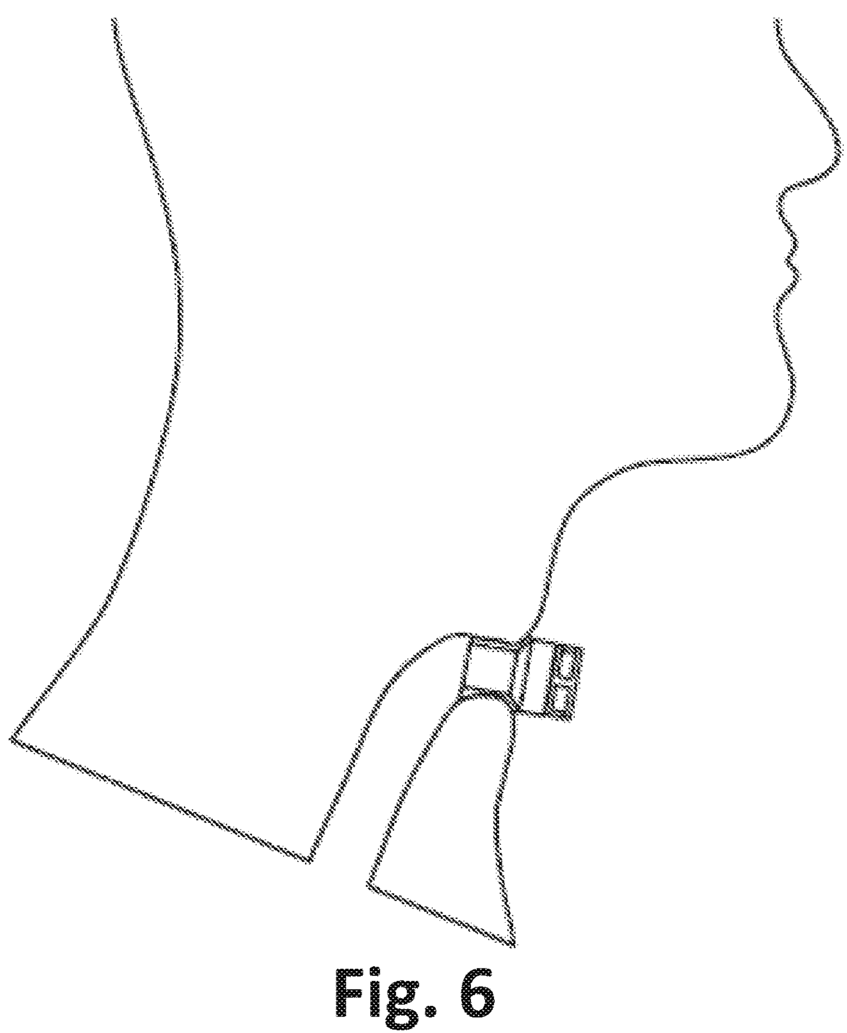
FIG. 6 illustrates a tracheostoma device holder according to an embodiment of the present invention in use.

According to still another embodiment, at least a portion of the exterior surface of both the radially expanding portion 40 and the tube portion 30 are provided with the deformable material 60. An example of this is illustrated in FIG. 5*a*-*c*. FIG. 5*a* shows a side view of the tracheostoma device holder 10 with a deformable material 60 according to this embodiment. FIG. 5*b* and FIG. 5*c* show the tracheostoma device holder 10 with a deformed deformable material 60. When the deformable material 60 is exemplified as a PVA foam, FIG. 5*b* and FIG. 5*c* may illustrate an expanded PVA foam, i.e. when the PVA foam 60 has been in contact with moisture. FIG. 6 illustrates a tracheostoma device holder 10, according to the embodiments disclosed in FIG. 5*a-c*, in use. It may be appreciated that even if FIG. 5*a-c* and FIG. 6 illustrate embodiments where a portion of the exterior surface of the fixation portion 20 is provided with the deformable material 60, embodiments where the total exterior surface of the fixation portion 20 is provided with a deformable material 60 may also be provided.

The dimensions of the deformable material 60 may be varied. The thicker and longer the deformable material 60, the more fixation. However, a larger deformable material 60, both length and thickness, may result in a higher pressure to which the tracheostoma device holder 10 remains fixated. Thus, the dimensions of the deformable material 60 may be chosen with care. The length L, illustrated in FIG. 5*a*, of the deformable material 60 may be chosen with regard to the length of the fixation portion 20. If the fixation portion 20 is short, the length L of the deformable material 60 is also short. However, with a longer fixation portion 20, the length L of the deformable material 60 may be increased and the length L may be longer than for a short fixation portion 20. Generally, the variation in length L of the deformable material 60 along axis 100 has more influence on the amount of fixation than the variation of the thickness of the deformable material 60. However, it may be appreciated that even a minimum length L of the deformable material 60 provided to the exterior surface of the fixation portion 20 may increase the tracheostoma device holder's 10 fixation inside a tracheostoma to withstand pressures up to coughing.

The exterior thickness of the deformable material may be varied. For example, if the deformable material 60 is exemplified as a PVA foam 60, the exterior thickness of the PVA foam may be between 3-10 mm. More preferably, the PVA foam exterior thickness may be between 5-6 mm. As previously stated, the thicker deformable material 60, e.g. a thicker PVA foam 60, the more secure fixation of the tracheostoma device holder 10 to the tracheostoma. However, a very thick deformable material 60, e.g. a very thick PVA foam, may exert a very high pressure to the tracheostoma. Thus, there is a trade-off between the amount of fixation and the risk on ischaemic damage. In order to eliminate, or at least reduce, the risk of ischemia and ischaemic damage on the tracheostoma walls when a PVA foam is used as a deformable material 60, the expanded PVA foam 60 may be compressed less than 60% of its total foam thickness when in use. Then, the tracheostoma device holder 10 will not exert pressures that will lead to ischaemic damage. A PVA foam exterior thickness of 5-6 mm provide both a safe and a secure fixation of the tracheostoma device holder 10 for variable tracheostoma shapes.

According to some embodiments, the deformable material 60 may have a Young's modulus slightly higher than that of the tracheal mucosa. Accordingly, when the tracheostoma device holder 10 is made out of silicone rubber, the deformable material 60 may have a stiffness that is much less than that of the tracheostoma device holder 10.

The deformable material 60 may be attached to the fixation portion 20 of the tracheostoma device holder 10 in several different ways. The deformable material 60 is secured to the tracheostoma device holder 10 such that the deformable material 60 will remain on the exterior surface of the fixation portion 20 while inserting, wearing and removing the tracheostoma device holder 10. According to some embodiments, the deformable material 60 may be attached directly to the fixation portion 20. The deformable material 60 may be attached by engaging the deformable material 60 with a mechanical attachment device located at the fixation portion 20. In other embodiments, the deformable material 60 may be glued directly to the fixation portion 20 of the tracheostoma device holder 10. In still other embodiments, the deformable material 60 may be attached to an attachment cylinder, wherein the attachment cylinder is configured to secure the deformable material 60 to said at least a portion of the exterior surface of the fixation portion 20. For example, a distal surface of the deformable material 60 may be attached to the attachment cylinder. The attachment cylinder may be attached to the deformable material 60 and the attachment cylinder may be placed around the fixation portion 20 of the tracheostoma device holder 10. The attachment cylinder may be, for example, a thin silicone rubber cylinder. For example, the attachment cylinder may be configured to secure the deformable material 60 to the exterior surface of the fixation portion 20 via an attachment device. The attachment device may be a kind of locking mechanism and may comprise, for example, protruding side attachments that may hook into mating attachments of the tracheostoma device holder 10. According to another example, the deformable material 60 may be glued to the attachment cylinder. As may be appreciated, the deformable material 60 may be attached to the exterior surface of the fixation portion 20 in several different ways, the described embodiments are only provided for illustrational purposes.

As seen in for example FIG. 6, the head portion 50 is extending distally from the tracheostoma device holder 10. The head portion 50 of the tracheostoma device holder 10 is configured to engage with, and thereby hold, a tracheostoma device. The head portion 50 may be configured to engage with a heat and moisture exchanger (HME). Additionally, or alternatively, the head portion 50 may be configured to engage with an automatic speaking valve.

Figure 7:
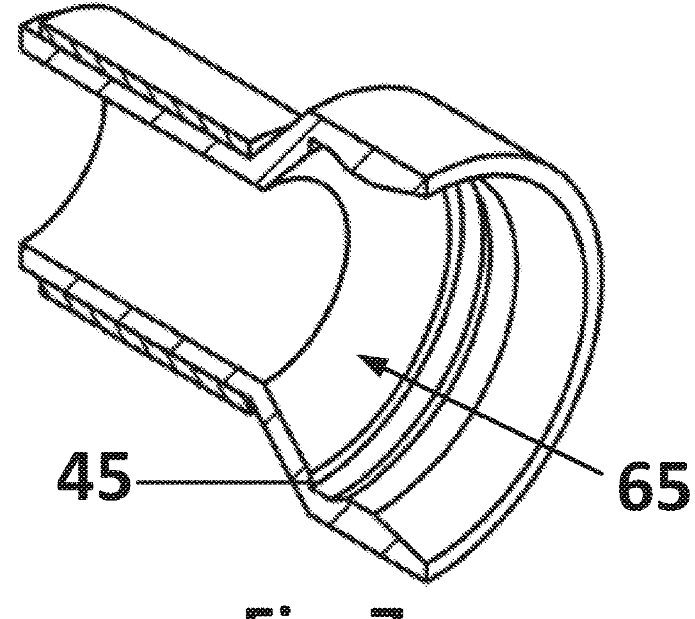
FIG. 7 is a cross-section view of a tracheostoma device holder according to an embodiment of the present invention.

The head portion 50 may engage with the tracheostoma device in different ways. According to one embodiment, the head portion 50 may comprise a tracheostoma device fitting 45. An example of a tracheostoma device fitting 45 is illustrated in FIG. 7. The tracheostoma device fitting 45 may be a tubular tracheostoma device fitting 45. The tracheostoma device fitting 45 comprises a through passage 65, extending through the tracheostoma device holder 10. Preferably, the tracheostoma device fitting 45 may be concentric with the through hole 65. The tubular tracheostoma device fitting 45 may be configured to receive the tracheostoma device, such that the tracheostoma device may be securely fastened to the tracheostoma device holder 10.

The tracheostoma device holder 10 may be attached to the tracheostoma of the user, such that the tubular portion 30 of the tracheostoma device holder 10 is inserted into the tracheostoma and a tracheostoma device, such as a speech valve, is connected to the tracheostoma device fitting 45 in a known manner.

The tracheostoma device holder 10 provided herein, with deformable material 60 on at least a portion of the fixation portion 20, ensures comfort and safety during insertion and removal of the tracheostoma device holder 10 to the tracheostoma of a person. The tracheostoma device holder 10 provides a sealing function and an airtight fixation of a tracheostoma device in the tracheostoma opening without exerting excessive pressure on the trachea wall that may cause pain and ischemia. The provided tracheostoma device holder 10 makes it possible to provide fixation of a tracheostoma device also to tracheostoma of persons that do not have a prominent peristomal lip.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

The invention claimed is:

1. A tracheostoma device holder comprising:

a head portion comprising a distal end of the tracheostoma device holder, with the head portion provided with a distal opening formed in the distal end of the tracheostoma device holder and sized to receive and retain a tracheostoma device insertable into the distal opening;

a fixation portion connected to and extending in a proximal direction from the head portion to a proximal end of the tracheostoma device holder, with a proximal end of the fixation portion provided with a proximal opening;

a lumen formed through the tracheostoma device holder extending from the distal opening of the head portion to the proximal opening of the fixation portion; and a seal disposed on an exterior surface of the fixation portion, where the seal is a hydrophilic foam adapted to expand when exposed to moisture;

wherein the fixation portion and the seal are insertable together into a tracheostoma such that the seal is adapted to attract moisture present in exhaled air and mucus expand to fixate the tracheostoma device holder to tissue of the tracheostoma.

2. The tracheostoma device holder of claim 1, wherein the seal, when expanded, provides intratracheal fixation for the tracheostoma device holder inserted into the tracheostoma.

3. The tracheostoma device holder of claim 1, wherein the seal is an expandable foam comprising polyvinyl alcohol.

4. The tracheostoma device holder of claim 1, wherein the seal is disposed around an entire circumference of the exterior surface of the fixation portion.

5. The tracheostoma device holder of claim 1, wherein the fixation portion is a cylindrical tube that is connected to the head portion by a radially expanded portion located between the fixation portion and the head portion.

6. The tracheostoma device holder of claim 5, wherein the radially expanded portion tapers outwardly between the fixation portion to the head portion.

7. The tracheostoma device holder of claim 1, wherein the fixation portion has a first diameter and the head portion has a second diameter, and the second diameter is larger than the first diameter.

8. The tracheostoma device holder of claim 1, wherein the fixation portion is integrated with the head portion to provide the tracheostoma device holder as a single unit.

9. The tracheostoma device holder of claim 1, further comprising: a device fitting formed on an interior surface of the head portion, where the device fitting is adapted to secure the tracheostoma device within the head portion in alignment and concentric with a portion of the lumen extending through the fixation portion.

10. The tracheostoma device holder of claim 1, wherein the distal opening of the head portion is sized to receive an automatic speaking valve.

11. The tracheostoma device holder of claim 1, wherein the distal opening of the head portion is sized to receive a heat and moisture exchange unit.

12. The tracheostoma device holder of claim 1, wherein the fixation portion and the head portion of the tracheostoma device holder are formed of a silicone rubber having a first Young's modulus matching a Young's modulus of tracheal mucosa, and the seal has a second Young's modulus that is less than the first Young's modulus such that the seal is softer than the tracheostoma device holder.

13. The tracheostoma device holder of claim 1, wherein a length of the seal extends for less than a length of the tracheostoma device holder.

14. The tracheostoma device holder of claim 13, wherein the length of the seal terminates before a proximal end of the head portion.

15. The tracheostoma device holder of claim 1, wherein the fixation portion and the seal are insertable within the tracheostoma at the same time.

16. A tracheostoma device holder comprising:

a head portion having an opening sized to retain a tracheostoma device;

a fixation portion integrated as a monolithic unit with the head portion, where the fixation portion has a first diameter and the head portion has a second diameter, and the second diameter is larger than the first diameter;

a radially expanded portion attached between the first diameter of the fixation portion and the second diameter of the head portion;

a lumen formed through the tracheostoma device holder from the head portion through the fixation portion; and a seal disposed around an exterior surface of the fixation portion and around a portion of the radially expanded portion;

wherein the seal is formed of a hydrophilic foam such that when the fixation portion with the seal is inserted into the tracheostoma, the seal attracts moisture from air and mucus in a tracheostoma environment and expands to provide intratracheal fixation that fixates the tracheostoma device holder to tissue of a tracheostoma.

17. The tracheostoma device holder of claim 16, further comprising:

an adhesive baseplate attached relative to the fixation portion of the tracheostoma device holder.

18. The tracheostoma device holder of claim 16, wherein the seal is disposed around an entire exterior surface of the fixation portion.

19. The tracheostoma device holder of claim 16, wherein a length of the seal extends for less than a length of the tracheostoma device holder.

20. The tracheostoma device holder of claim 16, wherein the seal is adapted to expand to seal a space between a wall of the tissue of the tracheostoma and the fixation portion such that the seal is adapted to expand to conform to a shape of the tissue of the tracheostoma.

* * * * *